US006855336B2

(12) United States Patent
Chen et al.

(10) Patent No.: US 6,855,336 B2
(45) Date of Patent: *Feb. 15, 2005

(54) OMEPRAZOLE FORMULATION

(75) Inventors: Chih-Ming Chen, Davie, FL (US); Joseph Chou, Manassas, VA (US); Unchalee Kositprapa, Ft. Lauderdale, FL (US)

(73) Assignee: ANDRX Pharmaceuticals, Inc., Fort Lauderdale, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/712,505

(22) Filed: Nov. 13, 2003

(65) Prior Publication Data

US 2004/0131684 A1 Jul. 8, 2004

Related U.S. Application Data

(60) Division of application No. 09/763,831, filed as application No. PCT/US99/19847 on Aug. 27, 1999, now Pat. No. 6,733,778, which is a continuation-in-part of application No. 09/143,167, filed on Aug. 28, 1998, now Pat. No. 6,174,548.

(51) Int. Cl.[7] .............................. A61K 9/14; A61K 9/16
(52) U.S. Cl. ....................... 424/490; 424/489; 424/493; 424/497
(58) Field of Search ................................ 424/489, 490, 424/493, 497

(56) References Cited

U.S. PATENT DOCUMENTS

| | | | |
|---|---|---|---|
| 4,045,563 A | 8/1977 | Berntsson et al. | |
| 4,045,564 A | 8/1977 | Berntsson et al. | |
| 4,182,766 A | 1/1980 | Krasso et al. | |
| 4,255,431 A | 3/1981 | Junggren et al. | |
| 4,337,257 A | 6/1982 | Junggren et al. | |
| 4,359,465 A | 11/1982 | Ruwart | |
| 4,432,966 A | 2/1984 | Zeitoun et al. | |
| 4,508,905 A | 4/1985 | Junggren et al. | |
| 4,544,750 A | 10/1985 | Brandstrom et al. | |
| 4,620,008 A | 10/1986 | Brandstrom et al. | |
| 4,636,499 A | 1/1987 | Brandstrom et al. | |
| 4,686,230 A | 8/1987 | Rainer et al. | |
| 4,738,974 A | 4/1988 | Brandstrom et al. | |
| 4,786,505 A | 11/1988 | Lovgren et al. | |
| 4,840,799 A | 6/1989 | Appeigren et al. | |
| 4,853,230 A | 8/1989 | Lovgren et al. | |
| 5,045,321 A | 9/1991 | Makino et al. | |
| 5,093,132 A | 3/1992 | Makino et al. | |
| 5,093,342 A | 3/1992 | Tomoi et al. | |
| 5,178,867 A | 1/1993 | Guittard et al. | |
| 5,204,118 A | 4/1993 | Goldman et al. | |
| 5,244,670 A | 9/1993 | Upson et al. | |
| 5,288,506 A | 2/1994 | Spickett et al. | |

(List continued on next page.)

FOREIGN PATENT DOCUMENTS

| | | | |
|---|---|---|---|
| CA | 1129417 | 8/1982 | |
| CA | 1127158 | 7/1985 | |
| CA | 1234118 | 3/1988 | |
| CA | 1263119 | 11/1989 | |
| CA | 1264751 | 1/1990 | |
| CA | 1292693 | 12/1991 | |
| CA | 2083605 | 12/1991 | |
| CA | 1302891 | 6/1992 | |
| CA | 2046364 | 1/1993 | |
| CA | 1324758 | 11/1993 | |
| CA | 2140347 | 2/1994 | |
| CA | 2139653 | 12/1994 | |
| CA | 2170647 | 1/1996 | |
| CA | 2193681 | 1/1996 | |
| CA | 1338377 | 6/1996 | |
| CA | 2037101 | 3/1997 | |
| CA | 2166794 | 3/1997 | |
| CA | 2166483 | 9/1997 | |
| EP | 124495 | 7/1984 | |
| EP | 1010423 A2 | 6/2000 | |
| GB | 1234058 | 6/1971 | |
| KR | 9208161 B * | 9/1992 | ......... A61K/31/415 |
| WO | WO 85/03436 | 8/1985 | |
| WO | WO 95/01783 | 1/1995 | |
| WO | WO 95/10264 | 4/1995 | |
| WO | WO 95/12590 | 5/1995 | |
| WO | WO 96/01612 | 1/1996 | |
| WO | WO 96/01622 | 1/1996 | |
| WO | WO 96/01623 | 1/1996 | |
| WO | WO 96/02535 | 2/1996 | |
| WO | WO 96/24338 | 8/1996 | |
| WO | WO 96/24375 | 8/1996 | |
| WO | WO 98/40069 A2 * | 9/1998 | .......... A61K/31/44 |

OTHER PUBLICATIONS

L. Olbe, S.E. et al., Present Situation and Future Prospects of Medical Treatment., Gastrins and the Vagus, Academic Press p. 245–250, 1979.

Ekenved et al. Studies with H 168/68, a Novel Gastric Acid Secretion Inhibition., Gut, vol. 22, p. A877, No. 10, Oct. 1981.

Erik Fellenius et al., Substituted Benzimidazoles Inhibit Gastric Acid Secretion by Blocking (H++K+) ATPase, Nature, vol. 290, p. 159–161, Mar. 12, 1981.

Tore Lind, et al. Effect of Omeprazole—A Gastric Proton Pump Inhibitor on Pentagastrin Stimulated Acid Secretion in Man., Gut, vol. 24 p. 270–276, 1983.

(List continued on next page.)

*Primary Examiner*—Thurman K. Page
*Assistant Examiner*—S. Tran
(74) *Attorney, Agent, or Firm*—Hedman & Costigan, P.C.

(57) ABSTRACT

A stable pharmaceutical composition of omeprazole for oral administration which consists essentially of: (a) a core of Omeprazole or a pharmaceutically equivalent salt, a filler and an alkaline material selected from the group consisting of lysing and arginine; and (b) a single layer of coating on said core which comprises a layer of an enteric coating agent which is applied from an organic solvent based system.

6 Claims, No Drawings

U.S. PATENT DOCUMENTS

| | | | |
|---|---|---|---|
| 5,304,540 A | | 4/1994 | Blackburn et al. |
| 5,330,982 A | | 7/1994 | Tyers |
| 5,352,688 A | | 10/1994 | Kaminski |
| 5,362,424 A | | 11/1994 | Lee et al. |
| 5,385,739 A | | 1/1995 | Debregeas et al. |
| 5,389,664 A | | 2/1995 | Baile et al. |
| 5,399,700 A | | 3/1995 | Min et al. |
| 5,417,980 A | | 5/1995 | Goldman et al. |
| 5,433,959 A | | 7/1995 | Makino et al. |
| 5,508,041 A | | 4/1996 | Lee et al. |
| 5,518,730 A | | 5/1996 | Fuisz |
| 5,599,794 A | | 2/1997 | Eek et al. |
| 5,620,964 A | | 4/1997 | Roth et al. |
| 5,622,717 A | | 4/1997 | Fuisz |
| 5,637,320 A | | 6/1997 | Bourke et al. |
| 5,639,478 A | | 6/1997 | Makino et al. |
| 5,693,818 A | | 12/1997 | Von Unge |
| 5,753,265 A | | 5/1998 | Bergstrand et al. |
| 6,013,281 A | * | 1/2000 | Lundberg et al. ........... 424/468 |
| 6,096,340 A | | 8/2000 | Chen et al. |
| 2004/0166162 A1 | * | 8/2004 | Niecestro et al. ........... 424/472 |

OTHER PUBLICATIONS

K–Fr Sewin et al., Effect of Substituted Benzimidazoles on Acid Secretion in Isolated and Enriched Guinea Pig Parietal Cells., Gut, vol. 24 p. 557–560, Jun. 1983.

Haken Larsson et al., Inhibition of Gastric Acid Secretion by Omeprazole in the Dog and the Rat. Gastroenterology, vol. 85 p. 900–907, Oct. 1983.

Walter Londong et al. Dose–Response Study of Omeprazole on Meal Stimulated Gastric Acid and Gastrin Release., Gastroenterology, vol. 85 p. 1373–1378, Dec. 1983.

Stanislaw J., Effects of Omeprazole, a Substituted Benzimidazole, on Gastrointestinal Secretions, Serum Gastrin and Gastric Mucosal Blood Flow in Dogs., Gastroenterology, vol. 86 p. 71–77 Jan. 1984.

D.A. Henry et al., Omeprazole: Effects on Oxidative Drug Metabolism., British Journal of Clinical Pharmacology, vol. 18, p. 195–200, Aug. 1984.

B.K. Sharma et al. Optimal Dose of Oral Omeprazole for Maximal 24 Hour Decrease of Intragastric Acidity., Gut, vol. 25, p. 957–964, Sep. 1984.

H.P.M. Festen et al., Effect of Oral Omeprazole on Serum Gastrin and Serum Pepsinogen I Levels., Gastroenterology, vol. 87 p. 1030–1034, Nov. 1984.

Peter Prichard et al. Omeprazole: A Study of Its Inhibition of Gastric pH and Oral Pharmacokinetics After Morning or Evening Dosages., Gastroenterology, vol. 88, p. 64–69 Jan. 1985.

K.O. Borg and L. Olbe, Omeprazole—A Survey of Preclinical Data., Gastroenterology, p. 15–22, 37–51, 71–77, 79–93, 105–120, Jun. 1985.

50th Edition of Physician's Desk Reference p. 529–531, 1996.

K.O. Borg, and L. Olbe, Proceedings of the First International Symposium on Omeprazole Supplement to the Scandinavian Journal of Gastroenterology, pp. 11–17, 31–38, 54–56, 59–60, 75–78, 89–135, 179, 182–183, 187–195, 1996.

Sep. 23, 1994 Decision of the Korean Patent Office Regarding Korean Patent No. 55426 (with Certified English Translation).

* cited by examiner

OMEPRAZOLE FORMULATION

This application is a divisional application of Ser. No. 09/763,831 filed on Jul. 11, 2001, now U.S. Pat. No. 6,733,778 which a 371 of PCT/US99/19847 filed on Aug. 27, 1999, which is a continuation-in-part of U.S. patent application Ser. No. 09/143,167, filed Aug. 28, 1998, now U.S. Pat. No. 6,174,548.

BACKGROUND OF THE INVENTION

The present invention relates to a stable formulation of omeprazole. It is well known that omeprazole is sensitive to acidic conditions and after contact with an acid, omeprazole will degrade and will not function in its intended manner. Initially, alkaline materials were added to a core of omeprazole and later an enteric coating was applied over the core to prevent the omeprazole from contacting the acidic pH conditions of the stomach. This approach is satisfactory if the product is administered within a short time after it is manufactured but if the product is stored under ambient conditions, the acidic residue of the enteric coating appears to degrade the omeprazole before it is administered to a patient. To solve this problem, the prior art has used a separate layer of a coating agent to coat a pellet core which contains omeprazole and an alkaline material which is thereafter coated with the enteric coating. This technique is described in U.S. Pat. No. 4,786,505. In addition WO 96/24338 discloses the use of an in situ formed interlayer that is based on the reaction of an aqueous enteric coating material with an alkaline material in the core.

This dual layer coating technique requires the application of two separate functional coating operations which increases the length of the manufacturing process and the cost of the product. The applicants have surprisingly discovered a coating system which avoids the need to use a coating layer to separate the omeprazole core from the enteric coating layer in an omeprazole dosage form. The separate coating system is based on the combined use of an enteric coating agent which is applied to a pelletized core or a granular core of omeprazole as a suspension in a suitable solvent.

The applicants have also surprisingly discovered that arginine or lysine can be used as a pH stabilizing agent.

SUMMARY OF THE INVENTION

The present invention provides a novel stable pharmaceutical composition of omeprazole for oral administration which consists essentially of:
(a) a core of omeprazole or a pharmaceutically equivalent salt, a filler and an alkaline material selected from the group consisting of lysine and arginine; and
(b) a single layer of coating on said core which comprises a layer of an enteric coating agent applied from an organic based solvent coating system.

The core of the pharmaceutical composition can be in the form of a compressed tablet which is further comprised essentially of a surface active agent, and a binder. Alternatively, the pharmaceutical composition can have a pelleted core which is further comprised essentially of an inert core component, a surface active agent and a binder.

Accordingly, it is a primary object of this invention to provide a pharmaceutical dosage formulation of omeprazole which is stable upon prolonged storage, is stable when administered to a patient and is capable of providing the desired therapeutic effect.

It is also an object of this invention to provide a pharmaceutical dosage form of omeprazole which is bioequivalent to dosage forms of omeprazole which have an intermediate layer of an inert coating material.

It is also an object of this invention to provide a stable dosage form of omeprazole which may be produced without the need to provide an intermediate coating layer that separates the omeprazole containing core from the enteric coating layer.

These and other objects of the invention will become apparent from a review of the appended specification.

DETAILED DESCRIPTION OF THE INVENTION

The omeprazole formulation of the invention is preferably based on a core of omeprazole or pharmaceutically equivalent salt, a filler and an alkaline material selected from the group consisting of arginine or lysine; and a single layer of coating on said core which comprises a layer of an enteric coating agent applied from an organic solvent based system. The Omeprazole core can either be pelleted or tabletted as described herein.

In the case of both the pelleted form and the tabletted form of the core a filler is used. A filler is used as a granulation substrate. Sugars such as lactose, dextrose, sucrose, maltose, or microcrystalline cellulose and the like may be used as fillers in either the pellet or the granulation composition. In the case of the pelleted form the filler may comprise from 20 to 90 wt % and preferably 65–85 wt % based on the total weight of the drug layer composition. In the case of the tabletted form the filler may comprise from 20 to 60 wt % and preferably 20 to 40 wt % based on the total weight of the granulation. In the case of the tabletted form of the invention a tablet disintegrant may be added which comprises corn starch, potato starch, croscarmelose sodium, crospovidone and sodium starch glycolate in an effective amount. An effective amount which may be from 3 to 10 wt % based on the total weight of the granulation.

In the case of both the tabletted form and the pelleted form of the core an alkaline agent that is either lysine or arginine is used as a stabilizer. In the case of the tabletted form a level of from 20 to 60 wt % and preferably 30 to 55 wt % based on the weight of the granulation may be employed. In the case of the pelleted form a level of from 0.5 to 10 wt % and preferably 1 to 3 wt % based on the weight of the pellet may be employed.

In the case of both the pelleted form and the tabletted form of the invention an enteric coating agent is placed over the core. In both cases the enteric coating may comprise an acid resisting material which resists acid up to a pH of above about 5.0 or higher which is selected from the group consisting of cellulose acetate phthalate, hydroxypropylmethyl cellulose phthalate, polyvinyl acetate phthalate, carboxymethylethylcellulose, Eudragit L (poly(methacrylic acid, methylmethacrylate), 1:1 ratio; MW (No. Av. 135,000—USP Type A) or Eudragit S (poly(methacrylic acid, methylmethacrylate, 1:2 ratio MW (No. Av. 135,000—USP Type B) and mixtures thereof.

The enteric coating agent may also include an inert processing aid in an amount in the case of the tabletted form from 15 to 55 wt % and preferably 20 to 45 wt % based on the total weight of the acid resisting component and the inert processing aid. In the case of the pelleted form the inert processing aid is preferably in an amount from 5 to 50 wt % and most preferably 10–20 wt %. The inert processing aids include finely divided forms of talc, silicon dioxide, magnesium stearate etc. Typical solvents which may be used to apply the acid resisting component-inert processing aid mixture include isopropyl alcohol, acetone, methylene chloride and the like. Generally the acid resistant component-inert processing aid mixture will be applied from a 5 to 20 wt % of acid resisting component-inert processing aid mixture based on the total weight of the solvent and the acid resistant component-inert processing aid.

In the case of both the tabletted form and the pelleted form of the invention omeprazole or a pharmaceutically equivalent salt is used in the core. In the tabletted formulation the omeprazole may comprise from 5 to 70 wt % and preferably 10 to 30 wt % of the granulation. In the pelleted form the Omeprazole may comprise from 10 to 50 wt % and preferably 10 to 20 wt % of the drug layer composition.

A surface active agent is used in both the tabletted and the pelleted form of the invention. The surface active agent may be any pharmaceutically acceptable, non-toxic surfactant. Suitable surface active agents include sodium lauryl sulfate, polysorbate 20, polysorbate 40, polysorbate 60, polysorbate 80 and the like. The surface active agent may be present at a level of from 0.1 to 5 wt %. In the case of the tabletted form the surface active agent is preferably 0.20 to 2.0 wt % based on the total weight of the granulation. In the pelleted form the surface active agent is preferably 0.20 to 2.0 wt % of the total weight of the drug layer composition.

The binder is used in both the tabletted and the pelleted form of the invention. The binder may be any pharmaceutically acceptable, non-toxic pharmaceutically acceptable binder. The binder is preferably a water soluble polymer of the group consisting of polyvinyl alcohol, polyvinylpyrrolidone, methylcellulose, hydroxypropyl cellulose, hydroxymethyl cellulose and the like. A water soluble binder is preferred which is applied from an aqueous medium such as water at a level of from 0.1 to 10 wt % and preferably from 0.25 to 7.5 wt % of binder based on the total weight of the granulation.

In the case of the tabletted form of the invention a granulation is formed by contacting the alkaline agent, the omeprazole, the surface active agent and the binder with a medium which may comprise any low viscosity solvent such as water, isopropyl alcohol, acetone, ethanol or the like. When fluids such as water are employed, this will usually require a weight of fluid which is about three times the weight of the dry components of the coating composition.

After the granulation is formed and dried, the granulation is tabletted and the tablets are directly coated with the enteric coating agent. A color imparting agent may be added to the enteric coating agent mixture or a rapidly dissolving seal coat containing color may be coated over the enteric coating agent layer provided that the seal coat is compatible with and does not affect the dissolution of the enteric coating layer. The rapidly dissolving seal coat may comprise Opadry pink which comprises approximately 91 wt % hydroxypropyl methylcellulose (E-6), color and 9 wt % polyethylene glycol which is applied as a 8–15% w/w solution in purified water. In addition the color may be provided as Chromateric which is available from Crompton & Knowles. This product contains water, talc, $TiO_2$, triethyl citrate, propylene glycol, synthetic red iron oxide, potassium sorbate, xanthan gum, sodium citrate and synthetic yellow iron oxide. If desired, conventional sugar based seal coats may be used which contain FDA certified dyes.

In the case of a pelleted form the invention is preferably based on pellets having a core forming inert component which may comprise a starch or sugar sphere such as non-pareil sugar seeds having an average size of 14 to 35 mesh, preferably about 18 to 20 mesh. The core forming inert component is coated with a formulation which comprises Omeprazole, a surface active agent, a filler, an alkaline material that is either lysine or arginine and a binder, which are collectively referred to as the drug layer composition. The core forming inert component is employed at 1:1 to 5:1 and preferably from 2:1 to 3:1 weight ratio to the drug layer composition.

The cores are formed by spraying the non-pareil seeds with an aqueous or non-aqueous suspension which contains the alkaline agent, the omeprazole, the surface active agent and the binder. The suspension medium may comprise any low viscosity solvent such as water, isopropyl alcohol, acetone, ethanol or the like. When fluids such as water are employed, this will usually require a weight of fluid which is about seven times the weight of the dry components of the coating composition.

After the cores are dried, the cores are coated with the enteric coating agent. A color imparting agent may be added to the enteric coating agent mixture or a rapidly dissolving seal coat over the enteric coating agent layer provided that the seal coat is compatible with and does no affect the dissolution of the enteric coating layer.

DESCRIPTION OF THE PREFERRED EMBODIMENTS

Examples 1 to 5 describe a tabletted form of the invention and Example 6 describes a pelleted form of the invention.

EXAMPLE 1

Granulation

A granulation containing omeprazole is formed in a fluid bed coater using a top spray granulation forming suspension containing omeprazole, micronized to 95% less than 15 microns, 5% w/w of the total amount of L-arginine, polyvinyl pyrrolidone, sodium lauryl sulfate and purified water which is sprayed onto a mixture of microcrystalline cellulose, 95% w/w of the total amount of L-arginine and sodium starch glycolate. The formulation for making the granulation has the following composition:

| | |
|---|---|
| povidone, USP (Plasdone K90) | 100.0 g |
| sodium starch glycolate | 100.0 g |
| sodium lauryl sulfate, NF/USP | 6.0 g |
| microcrystalline cellulose (AvicelPH101) | 965.6 g |
| L-arginine, USP/FCC | 1020.0 g |
| omeprazole, USP (micronized) | 340.0 g |
| purified water, USP | 1100.0 g |

Tabletting

The granulation is tabletted into tablets containing 20 mg of omeprazole by first mixing the omeprazole granules with glyceryl monostearate:

| | |
|---|---|
| omeprazole granules | 118.0 g |
| glyceryl monostearate (Myvaplex) | 6.0 g |
| Tabletting tools: | 0.2812" |
| target weight: | 124 mg/tab |
| target hardness: | 7 Kp |
| LOD of granules: | less than 3% |

Enteric Coating

An enteric coating is applied to prepare enteric coated tablets as follows:

| | |
|---|---|
| omeprazole tablets (prepared above) | 124.0 g |
| hydroxypropyl methylcellulose phthalate | 14.7 g |
| talc | 4.2 g |
| acetyl tributyl citrate | 2.9 g |
| acetone | 148.0 g |
| isopropyl alcohol | 148.0 g |

The solid coating materials were dissolved in the acetone and isopropyl alcohol and this solution was coated onto the omeprazole tablets using a perforated pan Seal Coat A seal coat was applied to the enteric coated tablets as follows:

| | |
|---|---|
| Enteric coated tablet | 146.0 g |
| Opadry II pink | 4.5 g |
| Water | 450.0 g |

The seal coat was applied onto the enteric coated omeprazole tablets using a perforated pan coater.

EXAMPLE 2

Granulation

A granulation containing omeprazole is formed in fluid bed coater using a top spray granulation forming suspension containing omeprazole, micronized to 95% less than 15 microns, 2.68% w/w of the total amount of L-arginine, polyvinyl pyrrolidone, polysorbate 80 and purified water which is sprayed onto a mixture of microcrystalline cellulose and 95.0% w/w of the total amount of L-arginine. The formulation for making the granulation has the following composition:

| | mg/tablet |
|---|---|
| povidone, USP (Plasdone K90) | 5.88 |
| polysorbate 80 (Tween 80) | 0.58 |
| L-arginine, USP/FCC | 60.0 |
| omeprazole, USP (micronized) | 20.0 |
| microcrystalline cellulose (Avicel PH102) | 25.54 |
| purified water, USP | n/a |

Tabletting

The granulation is tabletted into tablets containing 20 mg of omeprazole by first mixing the omeprazole granules with glyceryl monostearate:

| | |
|---|---|
| omeprazole granules | 112.0 mg |
| glyceryl monostearate (Myvaplex) | 6.8 mg |
| crospovidone XL | 16.2 mg |
| Tabletting tools: | 0.2812" |
| target weight: | 135 mg/tab |
| target hardness: | 7 Kp |
| LOD of granules: | less than 3% |

Enteric Coating

An enteric coating was applied to prepare enteric coated tablets as follows:

| | |
|---|---|
| omeprazole tablets (prepared above) | 135.0 mg |
| Eudragit L30D-55 | 14.0 mg |
| color (Chromateric) | 7.0 mg |
| 1 M NaOH (to adjust pH to 5.0) qs | na |
| Purified water qs | na |

The solid coating materials were dispersed in the water and this mixture was coated onto the omeprazole tablets using a perforated pan.

EXAMPLE 3

Granulation

A granulation containing omeprazole is formed in fluid bed coater using a top spray granulation forming suspension containing omeprazole, micronized to 95% less than 15 microns, 5.0% w/w of the total amount of L-arginine, polyvinyl pyrrolidone, sodium lauryl sulfate and purified water which is sprayed onto a mixture of microcrystalline cellulose and 95.0% w/w of the total amount of L-arginine. The formulation for making the granulation has the following composition:

| | mg/tablet |
|---|---|
| povidone, USP (Plasdone K90) | 5.0 |
| sodium lauryl sulfate | 0.3 |
| L-arginine, USP/FCC | 60.0 |
| omeprazole, USP (micronized) | 10.0 g |
| microcrystalline cellulose (AvicelPH102) | 24.7 |
| purified water, USP | n/a |

Tabletting

The granulation is tabletted into tablets containing 10 mg of omeprazole by first mixing the omeprazole granules with glyceryl monostearate:

| | |
|---|---|
| omeprazole granules | 100.0 mg |
| glyceryl monostearate (Myvaplex) | 5.0 mg |
| sodium starch glycolate | 5.0 mg |
| Tabletting tools: | 0.2812" |
| target weight: | 110 mg/tab |
| target hardness: | 7 Kp |
| LOD of granules: | less than 3% |

Enteric Coating

The tablets were coated with the same enteric coating that was applied to the tablets in Example 2.

EXAMPLE 4

Granulation

A granulation containing omeprazole is formed in fluid bed boater using a top spray granulation forming suspension containing omeprazole, micronized to 95% less than 15 microns, 5.0% w/w of the total amount of L-arginine, polyvinyl pyrrolidone, sodium lauryl sulfate and purified water which is sprayed onto a mixture of microcrystalline cellulose and 95.0% w/w of the total amount of L-arginine.

The formulation for making the granulation has the following composition:

|  | mg/tablet |
|---|---|
| povidone, USP (Plasdone K90) | 5.88 |
| polysorbate 80 | 0.60 |
| L-arginine, USP/FCC | 60.0 |
| omeprazole, USP (micronized) | 20.0 |
| crospovidone XL | 5.88 |
| microcrystalline cellulose | 25.54 |
| purified water, USP | n/a |

Tabletting

The granulation is tabletted into tablets containing 20 mg of omeprazole by first mixing the omeprazole granules with glyceryl monostearate:

| omeprazole granules | 117.9 mg |
|---|---|
| glyceryl monostearate (Myvaplex) | 6.1 mg |
| Tabletting tools: | 0.2812" |
| target weight: | 124 mg/tab |
| target hardness: | 7 Kp |
| LOD of granules: | less than 3% |

Enteric Coating

The tablets were coated with the same enteric coating that was applied to the tablets in Example 1.

EXAMPLE 5

The granulation of Example 1 was prepared and tabletted into tablets containing 20.0 mg of omeprazole. These tablets were coated as follows:

Enteric Coating

An enteric coating was applied to prepare enteric coated tablets as follows:

| omeprazole tablets (prepared above) | 126.00 mg |
|---|---|
| Eudragit L30D-55 | 17.00 mg |
| 1M NaOH (to adjust pH to 5.0) qs | na |
| acetyl tributyl citrate | 1.70 mg |
| talc | 3.80 mg |
| polysorbate 80 | 1.50 mg |
| Purified water qs | na |

The solid coating materials were dispersed in the water and this mixture was coated onto the omeprazole tablets using a perforated pan. A seal coat was applied using the procedure of Example 1.

EXAMPLE 6

In the case of a pharmaceutical formulation with a pelleted omeprazole core, the core is comprised of omeprazole, a surface active agent, a filler, an alkaline material and a binder.

Omeprazole activated pellets (sodium free) are prepared as follows: 13.650 kg of Purified water is dispensed into a suitably sized stainless steel container. L-Arginine Base (0.210 kg), Lactose Anhydrous, NF (1.75 kg) and Povidone (Plasdone ®K-90) (0.056 kg) is added to the purified water while homogenizing at full speed (about 5,000 rpm). Homogenizing is continued until the materials are completely dissolved. Polysorbate 80, NF (0.044 kg) is added to the solution while homogenizing at a lower speed (700–3300 rpm) to avoid excess foaming.

The material is homogenized until dissolved completely. Half of the solution (7.855 kg) is transferred into a 5–10 gallon stainless steel container. The original container is hereafter referred to as "container A" and the new container is henceforth referred to as "container B." Micronized omeprazole 95% less than 15 microns (0.980 kg) is added to container A while homogenizing at a lower speed (700–3300 rpm) to avoid excess foaming. The Omeprazole is allowed to disperse into the solution completely and then homogenized for another 10 minutes. The homogenizer is replaced with a mechanical stirrer and the suspension is continuously stirred throughout the coating process. When approximately three fourth of the omeprazole suspension in container A is consumed, 0.980 kg of micronized omeprazole is added to container B while homogenizing at a lower speed (700–3300) to avoid excess foaming. The Omeprazole is allowed to disperse in the solution completely and homogenization is continued for another 10 minutes. The homogenizer is replaced with a mechanical stirrer and the suspension is continuously stirred throughout the coating process. 9.98 kg of sugar spheres are added to a fluidized bed coater and preheated until the product reaches 40–45° C. The drug suspension from containers A and B are sprayed onto the spheres. The atomization pressure is between 1.5 to 3.5 bar and the pump rate is 2–100 ml/min. The spray rate does not exceed 20 ml/min in the first two hours to avoid agglomeration of the sugar spheres. The coating suspension is transferred to a smaller container to facilitate stirring when the surface of the coating suspension reaches the stirring blade. After the coating suspension has been consumed the pump is stopped and the fluidization is continued in the fluidized bed coater with the heat off until the product temperature drops below 32° C.

The pellets are then transferred to a fluidized bed coater into a 50° C. oven (45–55° C.). The pellets are dried until the moisture content of the pellets is not more then 2.5%. The pellets are separated into different size fractions by using a SWECO Separator equipped with 14 and 24 mesh screens. The pellets are collected in doubled polyethylene lined plastic containers and stored with desiccant.

Enteric Coating Process 10.844 kg of isopropyl alcohol, USP is dispensed into a suitably sized stainless steel container. 10.844 kg of acetone is added to the isopropyl alcohol. 1.683 kg of hydroxypropyl methylcellulose phthalate (Hypromellose 55, Substitution type 200731) and cetyl alcohol, NF (0.084 kg) are added to the solution while homogenizing at full speed until all the materials are dissolved completely. The homegnizer is then removed and replaced with a mechanical stirrer.

Talc (1.683 kg) is added while stirring. The talc is mixed until fully dispersed in the solution and the mixing is continued throughout the entire coating process. A fluidized bed coater is preheated to 32° C. The omeprazole active pellets (11.550 kg) are loaded into the fluidized bed coater and preheated until the temperature reaches 30° C.

The coating suspension is sprayed on the pellets using a product temperature of 25–35° C., an atomization pressure of 1.5 to 3.0 bar and a pump rate of 200–300 ml/min. The coating suspension is transferred to a smaller container to facilitate stirring when the surface of the coating suspension reaches the stirring blade.

After the coating suspension has been consumed the coated pellets are dried in a fluidized bed coater for 20 minutes using the same coating conditions except lowering the atomization pressure to 2 bars or below. The coated pellets are discharged into double polyethylene bags. The pellets are separated into different size fractions by using a SWECO separator equipped with 14 and 24 mesh screens. The pellets which are larger than 14 mesh and smaller than 24 mesh are rejected. The pellets that passed through the 14 mesh and retained on the 24 mesh are retained in polyethylene bags.

Blending

Omeprazole enteric coated pellets (Sodium Free), blended are prepared as follows:

14.400 kg of omeprazole enteric coated pellets (Sodium free) are charged into a blender. Talc, USP (0.225 kg) is sprinkled on top of the pellet bed and then blended at 28 rpm for 5 minutes. 0.2 to 0.5 grams of each sample is withdrawn into separate vials from the blender. The blended pellets are unloaded into plastic containers lined with double polyethylene. The excess talc is screened off using a SWECO separator equipped with a 24 mesh screen. The pellets are collected in containers lined with double polyethylene bags and stored with desiccant.

Encapsulation

An encapsulation room is prepared in which the relative humidity is in the range of 35–65% and the temperature is in the range of 15–25° C. Omeprazole enteric coated pellets (Sodium Free) blended are encapsulated using the following equipment and guidelines. A capsule machine model MACOFAR MT-20 is prepared for the procedure placing the machine setting at 4, using capsule machine size part 1, capsule magazine 1. The target filled capsule weight is 457.15 mg. If the total weight is not within 3% of the target weight, further adjustment must be performed. Capsule fill verification is performed at twenty minutes intervals on ten individual capsules. Acceptable capsules are collected in containers lined with double polyethylene bags and placed under desiccant.

While certain preferred and alternative embodiments of the invention have been set forth for purposes of disclosing the invention, modifications to the disclosed embodiments may occur to those who are skilled in the art. Accordingly, the appended claims are intended to cover all embodiments of the invention and modifications thereof which do not depart from the spirit and scope of the invention.

What is claimed is:

1. A method for preparing a stable oral pharmaceutical dosage formulation which consists of:

(a) forming a pellet core consists of 10 to 50 weight percent based on the total weight of the core of omeprazole or a pharmaceutically acceptable salt, a surface active agent, a filler, a binder and 0.5 to 10 weight percent based on the total weight of the core of a pharmaceutically acceptable alkaline agent, wherein the alkaline agent is selected from the group consisting of lysine and arginine; and (b) applying an enteric coating directly onto the core without a separating layer wherein the enteric coating layer surrounds the core and consisting essentially of an enteric coating agent, 5 to 50 weight percent based on the total weight of the coating layer of an inert processing aid and optionally a plasticizer.

2. The method recited in claim 1 wherein the enteric coating layer is applied from an organic solvent based system.

3. The method recited in claim 1 wherein the step of forming the core further comprises the step of applying the core ingredients onto an inert core.

4. The method recited in claim 1 wherein the pharmaceutically acceptable alkaline agent is about 1 to about 3% of the total weight of the core.

5. The method recited in claim 1 wherein the inert processing aid is selected from the group consisting of talc, silicon dioxide and magnesium stearate.

6. The method recited in claim 5 wherein the inert processing aid is talc.

* * * * *